United States Patent
Stark et al.

(10) Patent No.: US 6,895,802 B2
(45) Date of Patent: May 24, 2005

(54) MEASURING GAS CELL FOR A DEVICE FOR MEASURING THE CONCENTRATION OF A PARAMAGNETIC GAS

(75) Inventors: Hartmut Stark, Stockelsdorf (DE); Alfred Kelm, Badendorf (DE); Günter Steinert, Bad Oldesloe (DE); Hans Hansmann, Barnitz (DE); Peter Dreyer, Pansdorf (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 0 days.

(21) Appl. No.: 10/679,892

(22) Filed: Oct. 6, 2003

(65) Prior Publication Data

US 2004/0083789 A1 May 6, 2004

(30) Foreign Application Priority Data

Nov. 2, 2002 (DE) .......................................... 102 51 130

(51) Int. Cl.[7] .............................................. G01N 27/74
(52) U.S. Cl. ........................ 73/25.02; 73/25.01; 73/23.2
(58) Field of Search ............................... 73/25.02, 23.2, 73/25.01

(56) References Cited

U.S. PATENT DOCUMENTS 3,584,499 A * 6/1971 Hummel ..................... 73/25.02
4,860,574 A * 8/1989 Maeda et al. ................. 324/204
6,430,987 B1   8/2002 Stark ........................... 73/25.02

FOREIGN PATENT DOCUMENTS

DE 100 37 380 A1   5/2001
WO WO 9812552 A1 * 3/1998 .......... G01N/27/74

* cited by examiner

Primary Examiner—Hezron Williams
Assistant Examiner—Rodney Frank
(74) Attorney, Agent, or Firm—McGlew and Tuttle, P.C.

(57) ABSTRACT

A highly compact measuring gas cell for a device for measuring the concentration of a paramagnetic gas on the basis of the change in the thermal conductivity of the paramagnetic gas, which is brought about by a change in the magnetic field. The measuring gas cell has a bottom plate (1) that carries a measuring element (1.4) for the detection of the thermal conductivity of the measured gas, electric leads, an electric measuring gas cell heater (1.2) and a temperature-dependent electric sensor element (1.3) for the detection of the temperature of the measuring gas cell. A channel plate (2) is cut out for the gas guide in the area of the measuring element (1.4) and around the measuring element (1.4). A cover plate (3), seals the measuring gas cell in the upward direction and has at least two holes for the inlet and outlet of the gas into and out of the gas guide of the channel plate (2).

20 Claims, 2 Drawing Sheets

MEASURING GAS CELL FOR A DEVICE FOR MEASURING THE CONCENTRATION OF A PARAMAGNETIC GAS

FIELD OF THE INVENTION

The present invention pertains to a measuring gas cell for a device for measuring the concentration of a paramagnetic gas in a gas sample.

BACKGROUND OF THE INVENTION

A prior-art device for measuring the concentration of a paramagnetic gas, especially oxygen, is described in DE 100 37 380 A1 (and U.S. Pat. No. 6,430,987 which is hereby incorporated by reference), and is characterized by a modulatable magnetic field source with an air gap, by a modulation source for sending a modulation signal to the magnetic field source, by a measuring element for sending a measured heat flow signal, which is arranged at least partially within the air gap and is heated by a power source to a working temperature, and by a filter means connected to the measuring element for separating fluctuations from the measured heat flow signal based on the modulation of the magnetic field, wherein the changing amplitude of the fluctuations based on the gas-specific change in the thermal conductivity is an indicator of the percentage of the paramagnetic gas in the gas sample. The measurement of the oxygen concentration is performed in the air gap of the electrically modulatable magnet system, which air gap is equipped with a measuring gas cell. For such a device, there is a need for a compact measuring gas cell with high quality of the measured signal.

SUMMARY OF THE INVENTION

The object of the present invention is to provide a measuring gas cell for a device for measuring the concentration of a paramagnetic gas, which said measuring gas cell is improved in terms of the quality of the measured signal and handling and is highly compact.

According to the invention, a measuring gas cell is provided for a device for measuring the concentration of a paramagnetic gas. The measuring gas cell comprises a plurality of layer-like, connected plate elements. A bottom plate carries a measuring element for the detection of the thermal conductivity of the measured gas, electric leads, an electric measuring gas cell heater and a temperature-dependent electric sensor element for the detection of the temperature of the measuring gas cell. A channel plate is cut out to provide a gas guide in the area of the measuring element and around the measuring element. A cover plate seals the measuring gas cell in the upward direction. The cover plate has at least two holes for the inlet and outlet of the gas into and out of the gas guide of the channel plate.

The leads and the measuring gas cell heater may be covered by the non-cut-out area of the channel plate. The measuring element may have a microstructured heating element and a complementary, microstructured, temperature-dependent measuring element for the measured gas. The measuring element may be applied to an anesthetic-resistant membrane made preferably of silicon nitride.

In the direction of the flow of the measured gas, the measuring element may have at least one microstructured, temperature-dependent measuring element each in front of and behind a microstructured heating element arranged at right angles to the direction of gas flow for the determination of the velocity of flow of the measured gas from the measured signal difference of the microstructured, temperature-dependent measuring elements.

The bottom, channel and cover plates may be made so as to consist of a ceramic material, especially aluminum oxide.

The measuring element may be arranged at a spaced location from the bottom plate by means of spacer elements. With this arrangement two gaps of approximately equal size ate formed above and under the measuring element on the side facing the gas guide for the gas exchange of the measured gas to the measuring element. The gas exchange takes place essentially by diffusion.

The measuring gas cell according to the invention is especially useful for measurement of oxygen in an anesthesia apparatus or respirator. According to a further aspect of the invention, a process is provided for operating a respirator or an anesthesia apparatus including the steps of providing a measuring gas cell as a plurality of layered connected plate elements. The elements are provided as a bottom plate, a channel plate and a cover plate. The bottom plate carries a measuring element for the detection of the thermal conductivity of the measured gas, electric leads, an electric measuring gas cell heater and a temperature-dependent electric sensor element for the detection of the temperature of the measuring gas cell. The channel plate is cut out to provide a gas guide in the area of the measuring element and around the measuring element. The cover plate seals the measuring gas cell in the upward direction. The cover plate has at least two holes for the inlet and outlet of the gas into and out of the gas guide of the channel plate.

One essential advantage of the present invention arises from the fact that the measuring gas cell is made in a highly compact form from a plurality of individual, assembled and functionally cooperating, layer-like plate elements. As a result, accurate positioning of the measuring gas cell in a narrow air gap of a magnetic field source of a device for measuring the concentration of a paramagnetic gas, which said air gap measures only a few mm, is possible. Furthermore, relatively high and homogeneous magnetic flux density values can be reached in the air gap with the measuring gas cell due to the highly compact design in terms of the electric power consumption for the magnetic field generated, so that the quality of the measured signal as a whole is improved.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
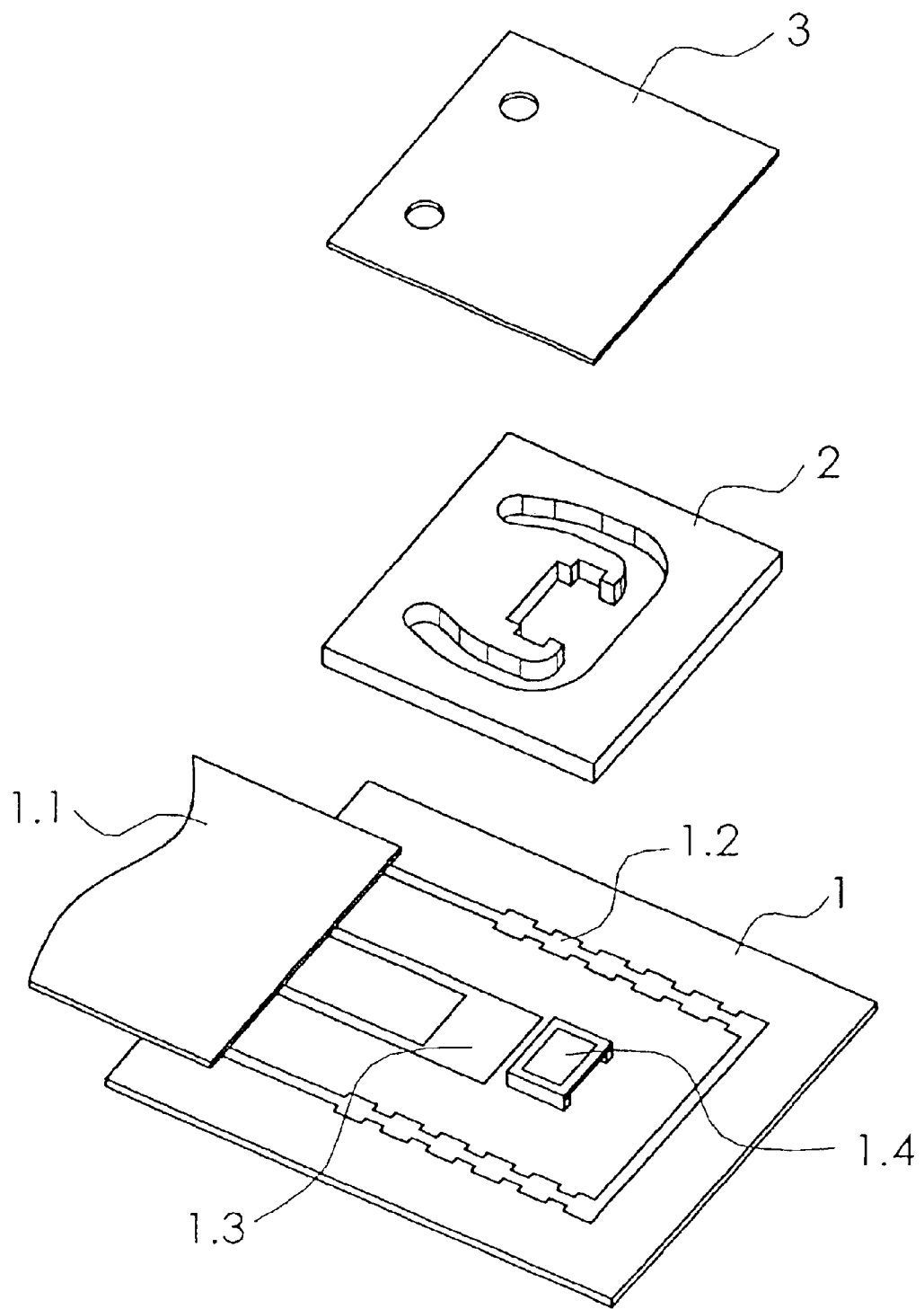
FIG. 1 is an exploded perspective view of a measuring gas cell for a device for measuring the concentration of a paramagnetic gas.
Figure 2:
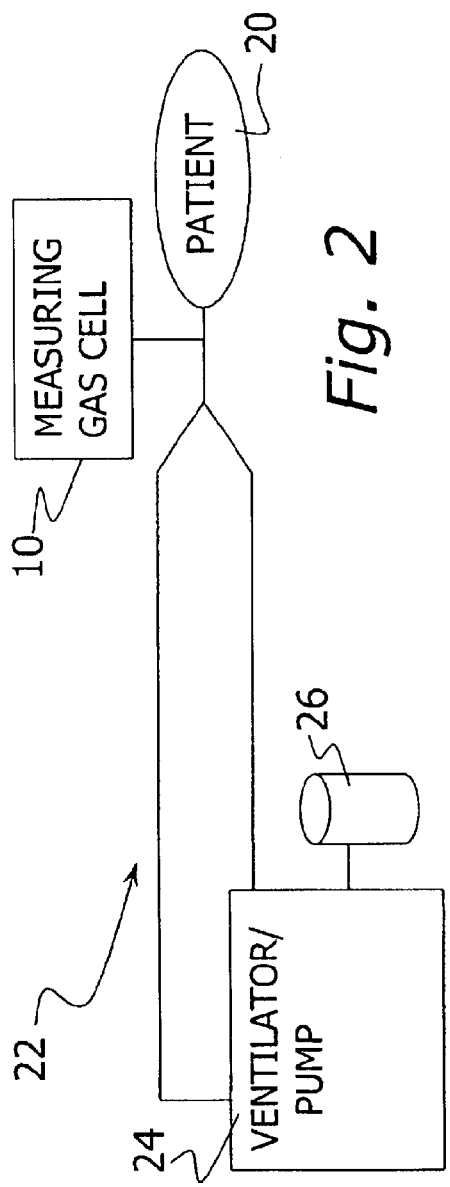
FIG. 2 is a schematic view showing the measuring gas cell used for measurement of oxygen in a respirator.
Figure 3:
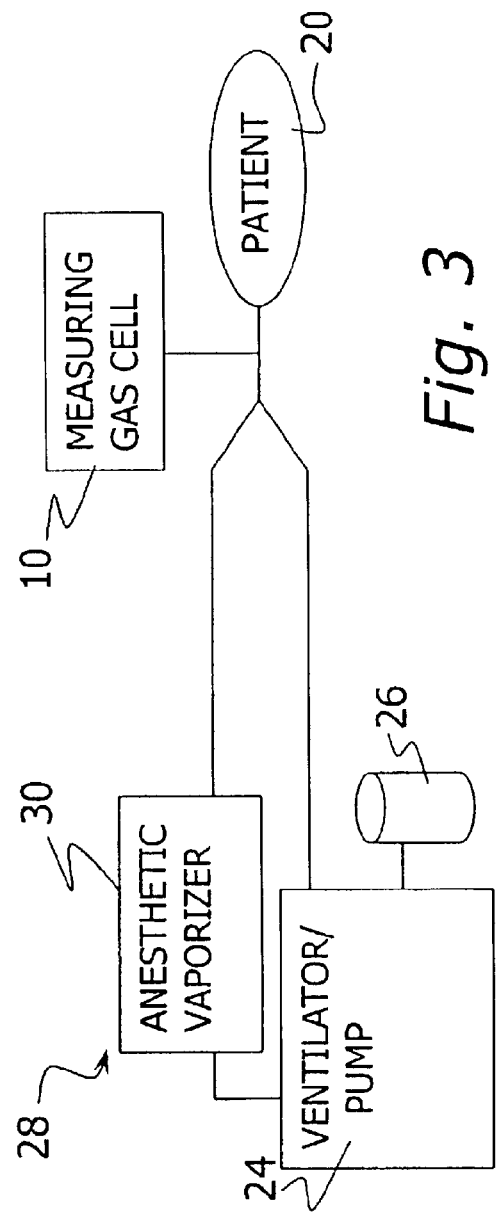
FIG. 3 is a schematic view showing the measuring gas cell used for measurement of oxygen in an anesthesia apparatus.

Referring to the drawings in particular, FIG. 1 shows a three-dimensional view of the individual layer-like plate elements of the measuring gas cell, which functionally cooperate in the assembled state. In the example, the measuring gas cell has a width and length of about 20 mm each and a thickness of only about 2 mm in the assembled state. The bottom plate 1 as well as the channel plate 2 and the cover plate 3 preferably consist of a ceramic material, especially aluminum oxide. On the one hand, ceramic material does not interfere with the external magnetic field applied, which is especially advantageous for measuring the oxygen concentration in the breathing gas in the case of use in an anesthesia apparatus. The bottom plate 1, the channel plate 2 and the cover plate 3 are connected by means of an adhesive such that the measured gas, which consists, in general, of the paramagnetic gas to be measured in a mixture with other gases, flows in the gas guide of the channel plate 2 sealed toward the outside, i.e., toward the environment. The bottom plate 1 is the carrier for the electric leads, which join the measuring gas cell in a flexible conductor strip 1.1. The bottom plate 1 has the electric components: measuring gas cell heater 1.2, comprising 12 heating resistors in the example, a temperature-dependent sensor element 1.3 for detecting the temperature of the measuring gas cell, and a measuring element 1.4, which is called a "measuring chip" for short.

The galvanic separation of the microstructured heating and measuring circuits is performed on the membrane of the measuring chip. The heating circuit, shown in the figure, on the bottom plate 1 of the measuring gas cell with the measuring gas cell heater 1.2 is used only for thermostatting, with a PTC temperature sensor as the temperature-dependent sensor element 1.3, the cell for stabilizing the working point and—what is even more important—for preventing the condensation of the measured gas.

The channel plate 2 is cut out for the gas guide in the area of the measuring chip and around the latter such that the measuring gas is led past the measuring chip, and direct effects on the temperature-dependent measured signal of the measuring chip due to the flowing past of the measured gas are very extensively avoided. After the introduction of the measuring chip on the bottom plate 1, the individual plate elements are mounted in an anesthetic-resistant manner by means of an adhesive, the electric leads and the measuring gas cell heater 1.2 being arranged such that they are essentially covered by the channel plate 2 in order to prevent a direct contact with the measured gas. The measuring element 1.4, called a "measuring chip" here, is located in a cutout of the channel plate 2 adjacent to the gas guide proper and is connected to the leads on the bottom plate 1 by bonding there. To make possible the entry of the gas to the top side and the underside of the measuring chip, the latter is arranged by means of spacer elements at such a spaced location from the bottom plate 1 that two flow gaps of approximately equal size, measuring about 0.3 mm, are formed on the side facing the gas guide above and below the measuring chip, and an exchange of gas takes place in the flow gaps from the measured gas to the measuring chip predominantly by means of diffusion. The measuring chip has at least one microstructured heating element, not shown in the figure, and preferably a plurality of microstructured, temperature-dependent measuring elements, which are arranged in the immediate vicinity and are likewise not shown, so that the temperature-dependent measured signal of the microstructured measuring elements also changes as a function of the concentration of the paramagnetic gas to be measured based on the accompanying change in the thermal conductivity, and the temperature-dependent measured signal is thus an indicator of the concentration of the paramagnetic gas. Since the measuring chip with its components is preferably applied to a membrane made especially of silicon nitride, the mobility of the components in the magnetic field is extensively reduced, and an effect on the measured signal is avoided. The measuring sensitivity is markedly increased by the use of a plurality of microstructured measuring elements with thermal transitions (thermopile) in the measuring chip.

Due to the arrangement of a microstructured, temperature-dependent measuring element each in front of and behind a microstructured heating element arranged at right angles to the direction of gas flow, the velocity of gas flow at the measuring chip can be additionally determined from the signal difference within limits set by the system, so that flow-related disturbances in the measurement can be eliminated or mitigated by a suitable calculation.

The cover plate 3 seals the measuring gas cell upwardly and outwardly and has at least two holes for the inlet and outlet of the gas into and out of the gas guide of the channel plate 2. The measured gas is fed into the measuring gas cell generally designated 10, e.g., from the breathing gas flow in an anesthesia apparatus 28 or respirator 22 by means of a pump or ventilator 24. The respirator 22 may have a fresh breathing gas source 26. The anesthesia apparatus 28 may include an anesthetic vaporizer 30 as well as a connection to a fresh breathing gas source 26 or a connection to another anesthetic gas source (not shown). The respirator 22 and anesthesia apparatus 28 may be used by a patient 20.

Due to its planar structure, the measuring gas cell described makes possible a small overall height of up to about 2 mm, as a consequence of which high and homogeneous magnetic flux density values can be reached in the air gap with the measuring gas cell relative to the electric power consumption for the magnetic field to be applied, so that the quality of the measured signal for the paramagnetic gas concentration measurement is markedly improved.

While specific embodiments of the invention have been shown and described in detail to illustrate the application of the principles of the invention, it will be understood that the invention may be embodied otherwise without departing from such principles.

What is claimed is:

1. A measuring gas cell for a device for measuring the concentration of a paramagnetic gas, the measuring gas cell comprising:

a bottom plate carrying a measuring element for the detection of the thermal conductivity of the measured gas, electric leads, an electric measuring gas cell heater and a temperature-dependent electric sensor element for the detection of the temperature of the measuring gas cell;

a channel plate with a cut out forming a gas guide in the area of the measuring element and around the measuring element; and a cover plate sealing the measuring gas cell in the upward direction, said cover plate having at least two holes for the inlet and outlet of the gas into and out of the gas guide of the channel plate, said bottom plate, said channel plate and said cover plate being provided as connected layers.

2. A measuring gas cell in accordance with claim 1, wherein the leads and the measuring gas cell heater are covered by a non-cut-out area of the channel plate.

3. A measuring gas cell in accordance with claim 1, wherein the measuring element has at least one microstructured heating element and at least one complementary, microstructured, temperature-dependent measuring element for the measured gas.

4. A measuring gas cell in accordance with claim 2, wherein the measuring element has at least one microstructured heating element and at least one complementary, microstructured, temperature-dependent measuring element for the measured gas.

5. A measuring gas cell in accordance with claim 1, wherein the measuring element is applied to an anesthetic-resistant membrane made of silicon nitride.

6. A measuring gas cell in accordance with claim 3, wherein in the direction of the flow of the measured gas, the measuring element has at least one microstructured, temperature-dependent measuring element each in front of and behind a microstructured heating element arranged at right angles to the direction of gas flow for the determination of the velocity of flow of the measured gas from the measured signal difference of the microstructured, temperature-dependent measuring elements.

7. A measuring gas cell in accordance with claim 5, wherein in the direction of the flow of the measured gas, the measuring element has at least one microstructured, temperature-dependent measuring element each in front of and behind a microstructured heating element arranged at right angles to the direction of gas flow for the determination of the velocity of flow of the measured gas from the measured signal difference of the microstructured, temperature-dependent measuring elements.

8. A measuring gas cell in accordance with claim 1, wherein the bottom plate, channel plate and cover plate consist essentially of a ceramic material.

9. A measuring gas cell in accordance with claim 1, wherein the bottom plate, channel plate and cover plate consist essentially of aluminum oxide.

10. A measuring gas cell in accordance with claim 1, wherein the measuring element is arranged at a spaced location from the bottom plate by means of spacer elements, so that two gaps of approximately equal size are formed above and under the measuring element on the side facing the gas guide for the gas exchange of the measured gas to the measuring element, which takes place essentially by diffusion.

11. A method of using a measuring gas cell for a device for measuring the concentration of a paramagnetic gas, comprising:

providing a bottom plate carrying a measuring element for the detection of the thermal conductivity of the measured gas, electric leads, an electric measuring gas cell heater and a temperature-dependent electric sensor element for the detection of the temperature of the measuring gas cell;

providing a channel plate with a cut out forming a gas guide in the area of the measuring element and around the measuring element;

providing a cover plate sealing the measuring gas cell in the upward direction, said cover plate having at least two holes for the inlet and outlet of the gas into and out of the gas guide of the channel plate;

connecting the bottom plate, the channel plate and the cover plate as layers to form the measuring gas cell;

measuring oxygen in an anesthesia apparatus or respirator using the measuring gas cell.

12. A method in accordance with claim 11, wherein the leads and the measuring gas cell heater are covered by the non-cut-out area of the channel plate.

13. A method in accordance with claim 11, wherein the measuring element has at least one microstructured heating element and at least one complementary, microstructured, temperature-dependent measuring element for the measured gas.

14. A method in accordance with claim 12, wherein the measuring element has at least one microstructured heating element and at least one complementary, microstructured, temperature-dependent measuring element for the measured gas.

15. A method in accordance with claim 11, wherein the measuring element is applied to an anesthetic-resistant membrane made of silicon nitride.

16. A method in accordance with claim 13, wherein in the direction of the flow of the measured gas, the measuring element has at least one microstructured, temperature-dependent measuring element each in front of and behind a microstructured heating element arranged at right angles to the direction of gas flow for the determination of the velocity of flow of the measured gas from the measured signal difference of the microstructured, temperature-dependent measuring elements.

17. A measuring gas cell in accordance with claim 15, wherein in the direction of the flow of the measured gas, the measuring element has at least one microstructured, temperature-dependent measuring element each in front of and behind a microstructured heating element arranged at right angles to the direction of gas flow for the determination of the velocity of flow of the measured gas from the measured signal difference of the microstructured, temperature-dependent measuring elements.

18. A method in accordance with claim 11, wherein the bottom plate, channel plate and cover plate consist essentially of a ceramic material.

19. A method in accordance with claim 11, wherein the bottom plate, channel plate and cover plate consist essentially of aluminum oxide.

20. A method in accordance with claim 11, wherein the measuring element is arranged at a spaced location from the bottom plate by means of spacer elements, so that two gaps of approximately equal size are formed above and under the measuring element on the side facing the gas guide for the gas exchange of the measured gas to the measuring element, which takes place essentially by diffusion.

* * * * *